United States Patent
Schiff

(12) 
(10) Patent No.: US 8,348,874 B2
(45) Date of Patent: Jan. 8, 2013

(54) ADJUSTABLE KNEE ORTHOSIS

(76) Inventor: Robert A. Schiff, Humble, TX (US)

( * ) Notice: Subject to any disclaimer, the term of this patent is extended or adjusted under 35 U.S.C. 154(b) by 243 days.

(21) Appl. No.: 12/943,124

(22) Filed: Nov. 10, 2010

(65) Prior Publication Data

US 2011/0112452 A1     May 12, 2011

Related U.S. Application Data

(60) Provisional application No. 61/259,754, filed on Nov. 10, 2009.

(51) Int. Cl.
    *A61F 5/00*     (2006.01)
    *E05D 7/00*     (2006.01)

(52) U.S. Cl. .......................... 602/16; 16/221

(58) Field of Classification Search .................. 602/1, 5, 602/16, 26, 23; 49/188, 388, 397, 149, 381; 16/334, 221, 321, 368, 319, 369
See application file for complete search history.

(56) References Cited

U.S. PATENT DOCUMENTS

| | | | |
|---|---|---|---|
| 5,653,680 A * | 8/1997 | Cruz ............................... | 602/21 |
| 7,854,708 B2 * | 12/2010 | Tong et al. ........................ | 601/5 |
| 7,985,193 B2 * | 7/2011 | Thorsteinsson et al. ......... | 602/16 |
| 2007/0010772 A1 * | 1/2007 | Ryan ............................... | 602/26 |
| 2010/0268137 A1 * | 10/2010 | Bachmann et al. ............. | 602/16 |
| 2011/0071452 A1 * | 3/2011 | Auberger ........................ | 602/26 |

* cited by examiner

*Primary Examiner* — Loan Thanh
*Assistant Examiner* — Tarla Patel
(74) *Attorney, Agent, or Firm* — Conley Rose, P.C.

(57) ABSTRACT

A knee orthosis comprises an upper leg attachment and a lower leg attachment. In addition, the knee orthosis includes a hinge joint extending between the upper leg attachment and the lower leg attachment. The hinge joint includes an upper arm having a first end fixed to the upper leg attachment and a second end opposite the first end. The second end including a semi-spherical surface. Further, the hinge joint includes a lower arm having a first end fixed to the lower leg attachment and a second end opposite the first end. The second end including a semi-spherical surface that mates with the semi-spherical surface of the second end of the upper arm.

17 Claims, 7 Drawing Sheets

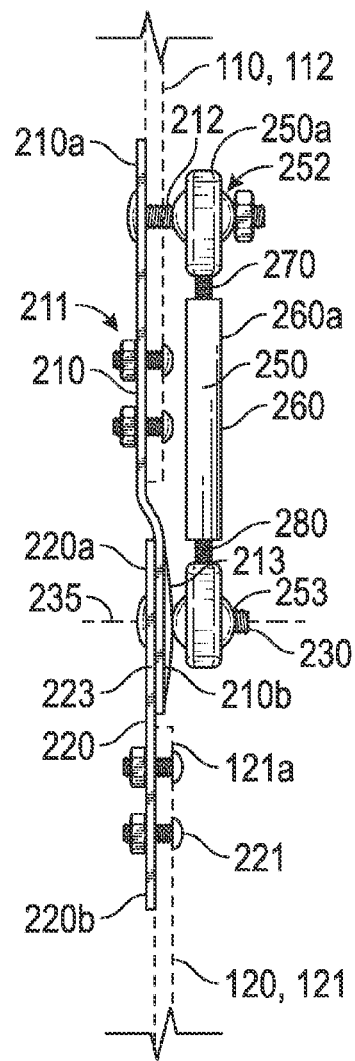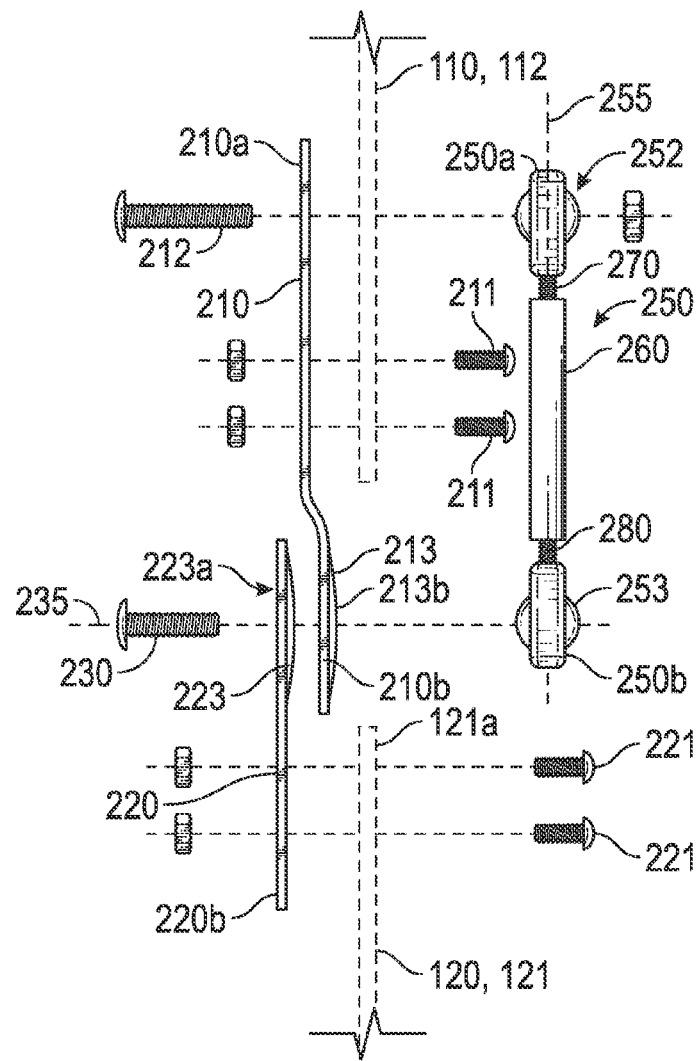
FIG. 7                              FIG. 8

ADJUSTABLE KNEE ORTHOSIS

CROSS-REFERENCE TO RELATED APPLICATIONS

This application claims benefit of U.S. provisional patent application Ser. No. 61/259,754 filed Nov. 10, 2009, and entitled "Adjustable Knee Orthosis," which is hereby incorporated herein by reference in its entirety.

STATEMENT REGARDING FEDERALLY SPONSORED RESEARCH OR DEVELOPMENT

Not applicable.

BACKGROUND

1. Field of the Invention

The invention relates generally to orthotics. More particularly, the invention relates to knee braces for correcting varus or valgus deformities of the knee.

2. Background of the Technology

Varus and valgus deformities are most often seen in patients suffering from osteoarthritis, but may also be present in other conditions such as lax ligaments. With a varus deformity, the knee joint is outwardly angulated, and with a valgus deformity, the knee joint is inwardly angulated.

There has been much research and effort put into creating more anatomical knee joints for knee orthoses. Unfortunately, many have inadequately addressed the problem of creating a joint that allows for adjustment of the angle of the knee in the frontal plane while providing for full range of motion of in the sagittal plane. Most current knee braces on the market only provide static corrective forces on the knee in the frontal plane. For example, a patient's knee may be in 15 degrees of angulation (varus or valgus) and a straight knee brace is forced onto the knee in an effort to hold the knee straight (i.e., correct the varus or valgus deformity). This tends to create an uncomfortable fit and more pressure along the areas of contact between the brace and the patient.

Those conventional knee braces that do allow for adjustment of varus or valgus deformities are not user adjustable. Instead, such braces are only adjustable by the health care provider via the use of tools, such as wrenches or screwdrivers. For example, one conventional knee brace includes a hinge that, when going into extension, increases the amount of corrective loading to the knee. However, that brace is not easily user adjustable and does not customize the knee joint to the individual's particular needs.

Accordingly, there remains a need in the art for ortheses and braces to correct varus and valgus deformities. Such ortheses would be particular well received if they were user adjustable.

BRIEF SUMMARY OF THE DISCLOSURE

These and other needs in the art are addressed in one embodiment by a knee orthosis. In an embodiment, the knee orthosis comprises an upper leg attachment. In addition, the knee orthosis comprises a lower leg attachment. Further, the knee orthosis comprises a hinge joint extending between the upper leg attachment and the lower leg attachment. The hinge joint includes an upper arm having a first end fixed to the upper leg attachment and a second end opposite the first end. The second end including a semi-spherical surface. The hinge joint also includes a lower arm having a first end fixed to the lower leg attachment and a second end opposite the first end. The second end including a semi-spherical surface that mates with the semi-spherical surface of the second end of the upper arm. Still further, the hinge joint includes a first pin extending laterally through the semi-spherical surface of the lower arm and the semi-spherical surface of the upper arm. The pin pivotally couples the upper arm to the lower arm. Moreover, the hinge joint includes a second pin extending laterally through the upper arm. The hinge joint also includes an extension coupling having a longitudinal axis, a first end pivotally and rotatably coupled to the first pin, and a second end pivotally and rotatably coupled to the second pin. The extension coupling is adapted to increase the axial distance between the first pin and the second pin.

These and other needs in the art are addressed in another embodiment by a knee orthosis. In an embodiment, the knee orthosis comprises an upper leg attachment. In addition, the knee orthosis comprises a lower leg attachment. Further, the knee orthosis comprises a hinge joint extending between the upper leg attachment and the lower leg attachment. The hinge joint includes an upper arm having a first end fixed to the upper leg attachment and a second end opposite the first end, the second end including an attachment plate. Still further, the hinge joint includes a lower arm having a first end fixed to the lower leg attachment and a second end opposite the first end. The second end including an attachment plate rotatably coupled to the attachment plate of the upper arm. The attachment plate of the upper arm includes an elongate slot, and the attachment plate of the lower arm includes a throughbore aligned with at least a portion of the elongate slot. Moreover, the hinge joint includes a first pin extending through the throughbore and the elongate slot. The hinge joint also includes an extension coupling having a longitudinal axis, a first end coupled to the first pin, and a second end pivotally and rotatably coupled to the upper arm. The extension coupling is adapted to move the first pin through the elongate slot.

Thus, embodiments described herein comprise a combination of features and advantages intended to address various shortcomings associated with certain prior devices, systems, and methods. The various characteristics described above, as well as other features, will be readily apparent to those skilled in the art upon reading the following detailed description, and by referring to the accompanying drawings.

BRIEF DESCRIPTION OF THE DRAWINGS

For a detailed description of the preferred embodiments of the invention, reference will now be made to the accompanying drawings in which:

FIG. 7 is a front view of the joint hinge of FIG. 2 in a "straight" position;

FIG. 8 is an exploded front view of the joint hinge of FIG. 2;

DETAILED DESCRIPTION OF SOME OF THE PREFERRED EMBODIMENTS

Figure 1:
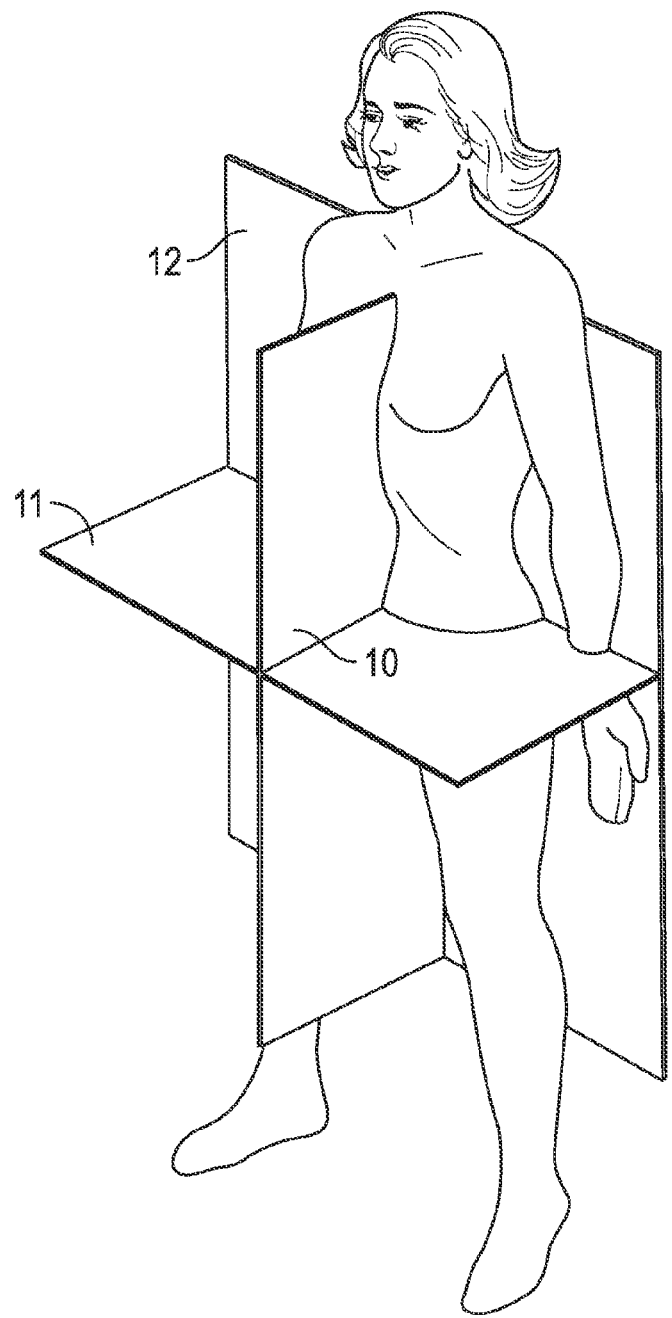
FIG. 1 is a perspective view of a human body illustrating the sagittal plane, transverse plane, and frontal plane.

The following discussion is directed to various embodiments of the invention. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

Certain terms are used throughout the following description and claims to refer to particular features or components. As one skilled in the art will appreciate, different persons may refer to the same feature or component by different names. This document does not intend to distinguish between components or features that differ in name but not function. The drawing figures are not necessarily to scale. Certain features and components herein may be shown exaggerated in scale or in somewhat schematic form and some details of conventional elements may not be shown in interest of clarity and conciseness.

In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through a direct connection, or through an indirect connection via other devices and connections. In addition, as used herein, the terms "axial" and "axially" generally mean along or parallel to a central or longitudinal axis (e.g., central axis of a body or a port), while the terms "radial" and "radially" generally mean perpendicular to the central or longitudinal axis. For instance, an axial distance refers to a distance measured along or parallel to the central axis, and a radial distance means a distance measured perpendicular to the central axis.

Referring briefly to FIG. 1, for purposes of this discussion, anatomical positions and movement are described with reference to the sagittal or median plane 10, the transverse plane 11, and the frontal or coronal plane 12. As is known in the art, the sagittal plane 10 is orthogonal to both the transverse plane 11 and the frontal plane 12, and passes from the top to the bottom of the body and separates the left and the right sides of the body. In addition, the transverse plane 11 is orthogonal to both the sagittal plane 10 and the frontal plane 12, and divides the body into upper and a lower halves. Further, the frontal plane 12 is orthogonal to both the sagittal plane 10 and the transverse plane 11, and divides the body into the forward (anterior) and the back (posterior).

Figure 2:
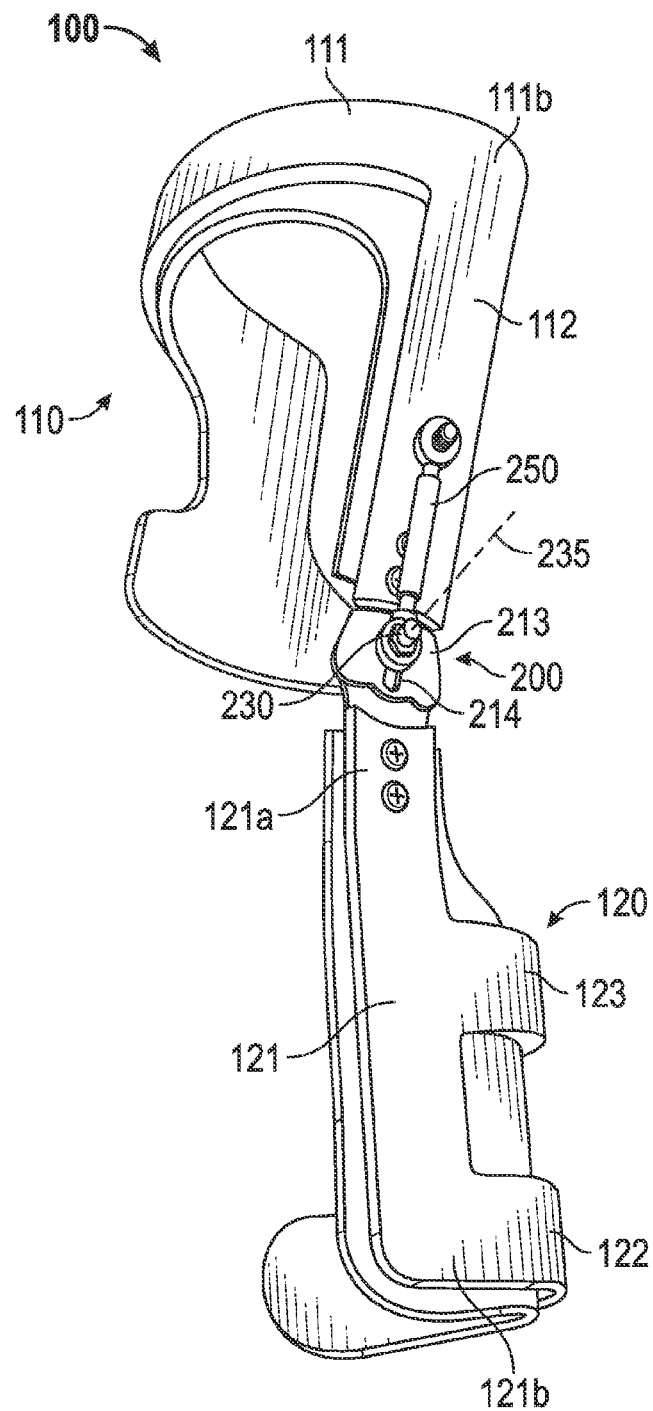
FIG. 2 is a perspective side view of an embodiment of a knee orthosis in accordance with the principles described herein.
Figure 3:
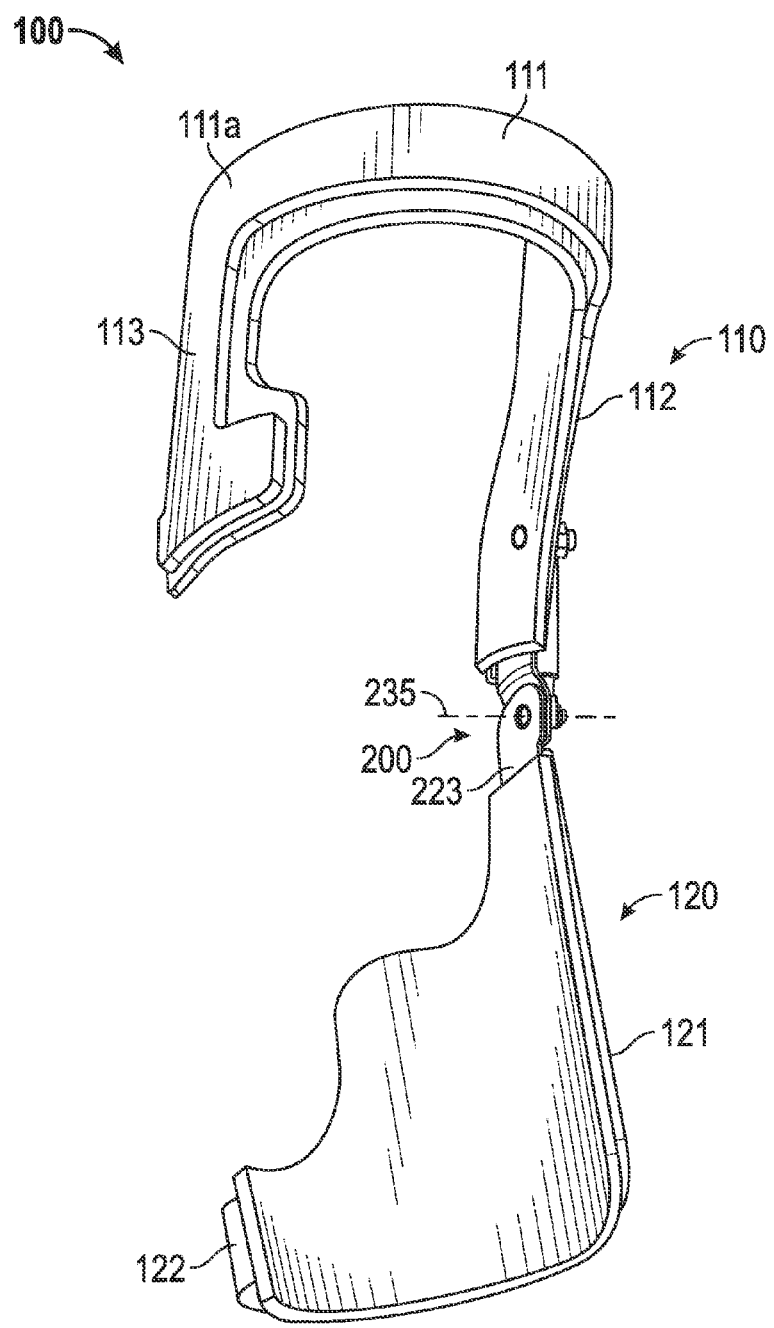
FIG. 3 is a perspective front view of the knee orthosis of FIG. 2.
Figure 4:
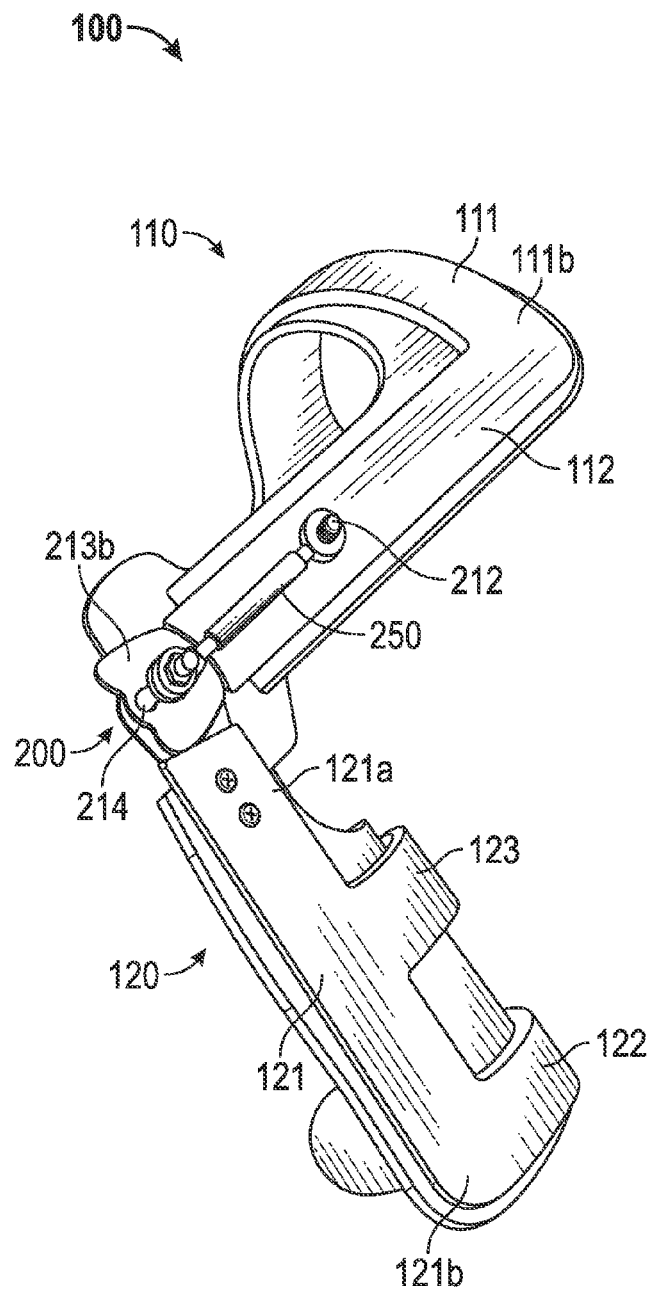
FIG. 4 is a perspective side view of the knee orthosis of FIG. 2 in a bent position.

Referring now to FIGS. 2-4, an embodiment of a knee orthosis or brace 100 in accordance with the principles described herein is shown. In general, a knee orthosis (e.g., knee orthosis 100) is an external orthopedic device or appliance that prevents or assists the flexion of the knee joint. In this embodiment, knee orthosis 100 includes an upper leg attachment member 110, a lower leg attachment member 120, and a user-adjustable hinge joint 200 that pivotally couples the upper leg attachment member 110 to the lower leg attachment member 120. Upper leg attachment 110 is designed to be secured to the portions of the patient's leg above the knee (e.g., patient's thigh), and lower leg attachment 120 is designed to be secured to the portion of the patient's leg below the knee (e.g., upper calf). Lower leg attachment member 120 may pivot relative to the upper leg attachment member 110 about a pivot axis 235 defined by a pivot pin 230 in hinge joint 200.

Leg attachment members 110, 120 are generally shaped to receive the upper portion of a patient's leg and the lower portion of the patient's leg, respectively. Specifically, upper leg attachment member 110 includes a ventral leg portion 111, an outer lateral extension 112, and an inner medial extension 113. Ventral leg portion 111 extends laterally across the front of the upper leg and has a first or medially inner end 111a disposed along the inner thigh of the patient, and a second or laterally outer end 111b opposite end 111a and disposed along the outer thigh of the patient. In this embodiment, ventral leg portion 111 is arcuate to generally conform to the convex shape of the front portion of the patient's thigh. Outer lateral extension 112 extends caudally along the outer lateral side of the upper leg from end 111b to hinge joint 200, and inner medial extension 113 extends caudally along the inner medial side of the upper leg from end 111a. Moving caudally or downward from ventral leg portion 111, lateral extensions 112, 113 taper slightly inward toward each other to conform to the shape of the laterally inner and outer portions of the thigh. In this embodiment, ventral leg portion 111, lateral extension 112, and medial extension 113 comprise a single piece that is monolithically formed (e.g., mold or cast as a single piece).

Lower leg attachment member 120 includes an outer lateral extension 121, a first or distal dorsal leg portion 122, and a second or proximal dorsal leg portion 123 dispose above or proximal to lower leg portion 122. Outer lateral extension 121 extends caudally along the outer lateral side of the lower leg, and includes a first or upper end 121a coupled to hinge joint 200 and a second or lower end 121b opposite end 121a and distal hinge joint 200. Lower dorsal leg portion 122 extends laterally from end 121b across the back of the patient's lower leg and calf, and upper dorsal leg portion 123 extends laterally from extension 121 across the back of the patient's lower leg and calf. In this embodiment, dorsal leg portions 122, 123 are each arcuate to generally conform to the convex shape of the dorsal portion of the patient's lower leg and calf. In this embodiment, lateral extension 121 and dorsal leg portions 122, 123 comprise a single piece that is monolithically formed (e.g., mold or cast as a single piece). The components of upper leg attachment member 110 and lower leg attachment member 120 (e.g., ventral leg portion 111, dorsal leg portions 122, 123, etc.) are strategically positioned to maintain the rigidity of knee orthosis 100 while resisting the inherent tendency of knee orthosis 100 to slide down on the patient's leg.

In general, attachment members 110, 120 may be formed from any suitable material(s) including, without limitation, metals and metal alloys (e.g., steel, aluminum, etc.), non-metals (e.g., polymers, etc.), composites (e.g., carbon fiber and epoxy matrix composite, etc.) or combinations thereof. However, leg attachment members 110, 120 preferably comprise relatively lightweight, durable materials such as plastic or composites. To enhance patient comfort, the interior of each attachment member 110, 120 that bears against the patient's leg preferably comprises a relatively soft padding.

Straps or other means such as Velcro may be used to securely fasten leg attachments 110, 120 to the patient's leg.

Referring now to FIGS. 5-10, an embodiment of user-adjustable hinge joint 200 is shown. Although hinge joint 200 was previously shown in knee orthosis 100, in general, hinge joint 200 may be used in any hinged knee orthosis or brace, and further, may be used in orthotic devices or braces for other joints such as the elbow. In this embodiment, hinge joint 200 comprises a first or upper arm 210 and a second or lower arm 220 rotatably coupled to arm 210. Hinge joint 200 is generally positioned on the lateral outer part of the patient's knee with upper arm 210 generally aligned with the femur and proximal to the knee joint, and lower arm 220 generally aligned with the tibia and fibula distal to the knee joint. Although hinge joint 200 is generally positioned on the lateral outer part of the patient's knee in this embodiment, in other embodiments, the hinge joint (e.g., hinge joint 200) may be positioned medially along the inside of the knee.

Upper arm 210 has a longitudinal axis 215, a first or upper end 210a distal lower arm 220, and a second or lower end 210b opposite end 210a and coupled to lower arm 220. Arm 210 is fixably attached to upper leg attachment member 110 with coupling members 211 that extend laterally through outer lateral extension 112 of upper leg attachment member 210 and arm 210. Thus, arm 210 does not move rotationally or translationally relative to upper leg attachment member 110. In this embodiment, each coupling member 211 is a bolt. In addition, a pin 212 extends laterally through outer lateral extension 112 and arm 210 proximal upper end 210a. As will be described in more detail below, pin 212 pivotally couples an extension assembly 250 to arm 210 and upper leg attachment member 110.

Figure 5:
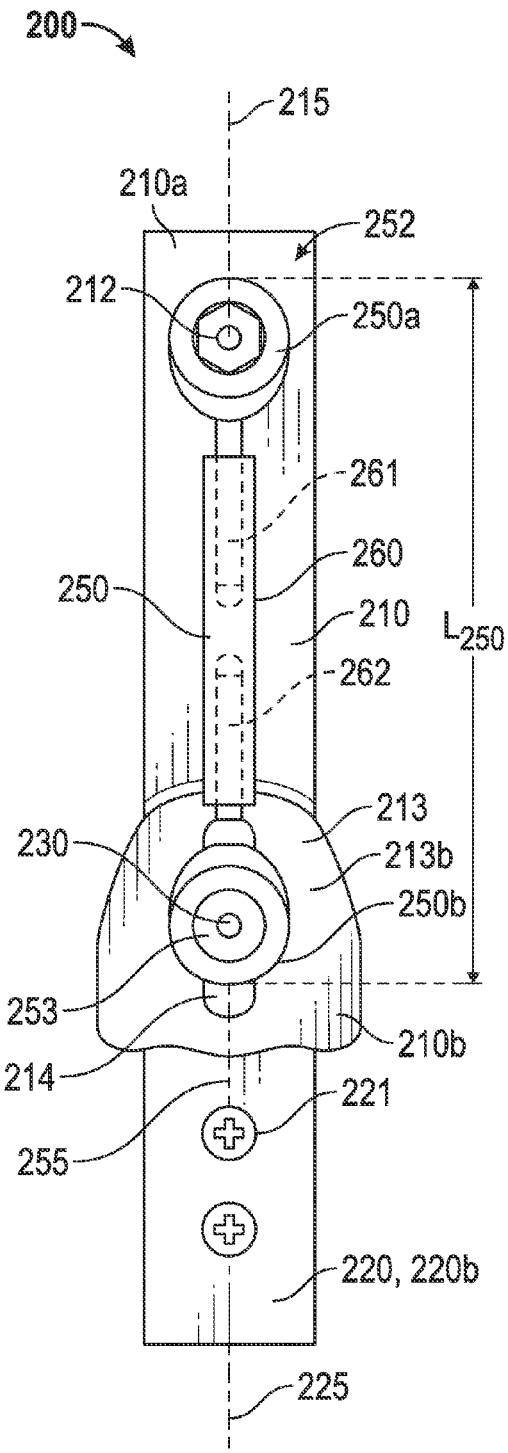
FIG. 5 is a laterally outer side view of the joint hinge of FIG. 2.
Figure 6:
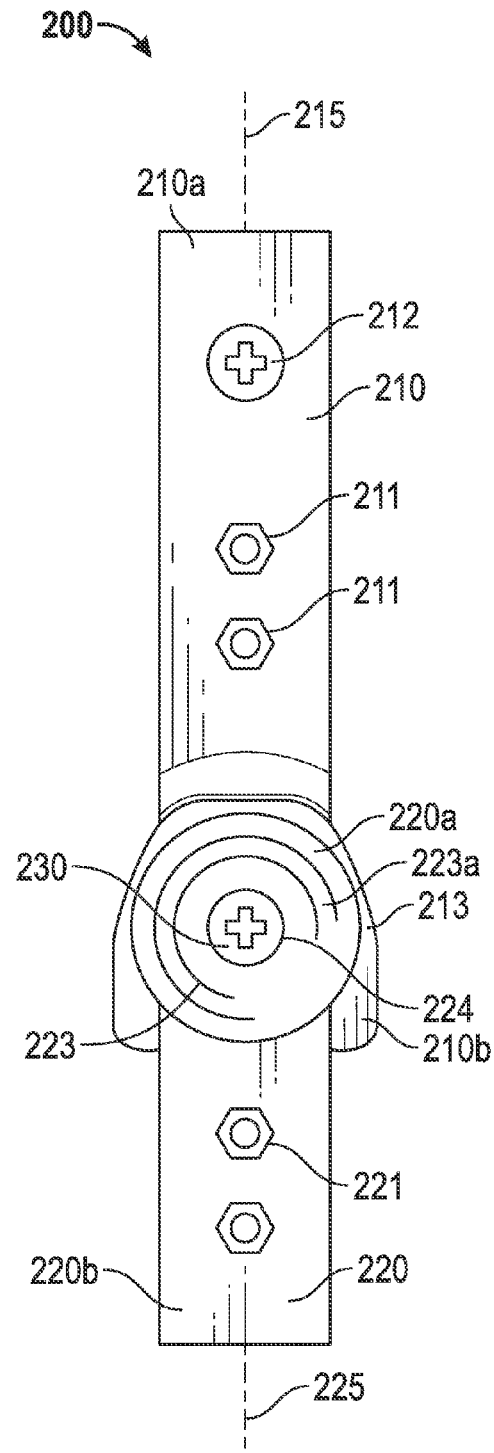
FIG. 6 is a laterally inner side view of the hinge joint of FIG. 2.

Lower end 210b of arm 210 comprises an attachment plate 213 with a medially inner, concave semi-spherical surface 213a and a laterally outer, convex semi-spherical surface 213b parallel to inner surface 213a. In addition, attachment plate 213 includes an elongate slot 214 extending laterally between surfaces 213a, 213b. As best shown in FIG. 5, slot 214 is a straight or linear slot that is aligned with longitudinal axis 215 in lateral side view.

Referring still to FIGS. 5-10, lower arm 220 has a longitudinal axis 225, a first or upper end 220a coupled to lower end 210b of upper arm 210, and a second or lower end 220b opposite end 210b and distal upper arm 210. Arm 220 is fixably attached to lower leg attachment member 120 with coupling members 221 that extends laterally through outer lateral extension 121 of lower leg attachment member 120 and arm 220. Thus, arm 220 does not move rotationally or translationally relative to lower leg attachment member 120. In this embodiment, each coupling member 221 is a bolt.

Upper end 220a of arm 220 comprises an attachment plate 223 with a medially inner, concave semi-spherical surface 223a and a laterally outer, convex semi-spherical surface 223b parallel to inner surface 223a. In addition, attachment plate 223 includes a central throughbore 224 extending laterally therethrough and generally aligned with a portion of slot 214.

Attachment plates 213, 223 are positioned in a nested arrangement with lower arm plate 223 received by upper arm plate 213 such that mating surfaces 213a, 223b are opposed one another. In particular, semi-spherical concave inner surface 213a of upper plate 213 has the same radius of curvature as semi-spherical convex outer surface 223b of lower plate 223. Pivot pin 230 extends through central bore 224 in lower plate 223 and elongate slot 214 in upper plate 223, thereby enabling upper arm 210, associated plate 213, and upper leg attachment member 110 to rotate or pivot relative to lower arm 220, plate 223, and lower leg attachment member 120 about central or longitudinal axis 235 of pivot pin 230. A friction reducing material or coating, such as Teflon® (e.g., Teflon® washer) is preferably positioned between plates 213, 223 to allow upper arm 210 and lower arm 220 to smoothly and easily rotate relative to each other about axis 235 generally in the sagittal plane.

Figure 9:
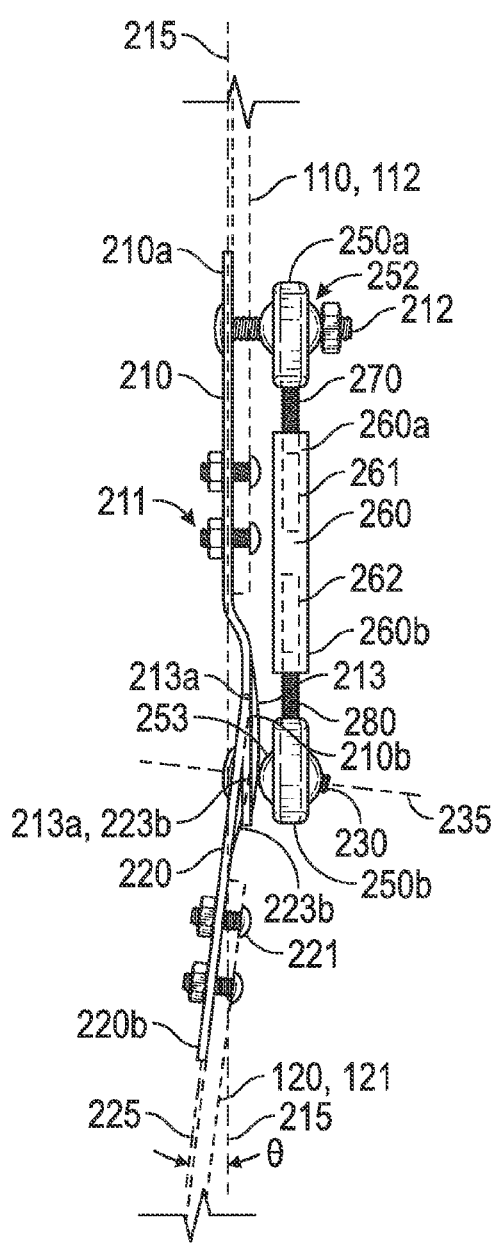
FIG. 9 is a front view the joint hinge of FIG. 2 with the extension assembly in an extended position and the lower arm angled medially inward.
Figure 10:
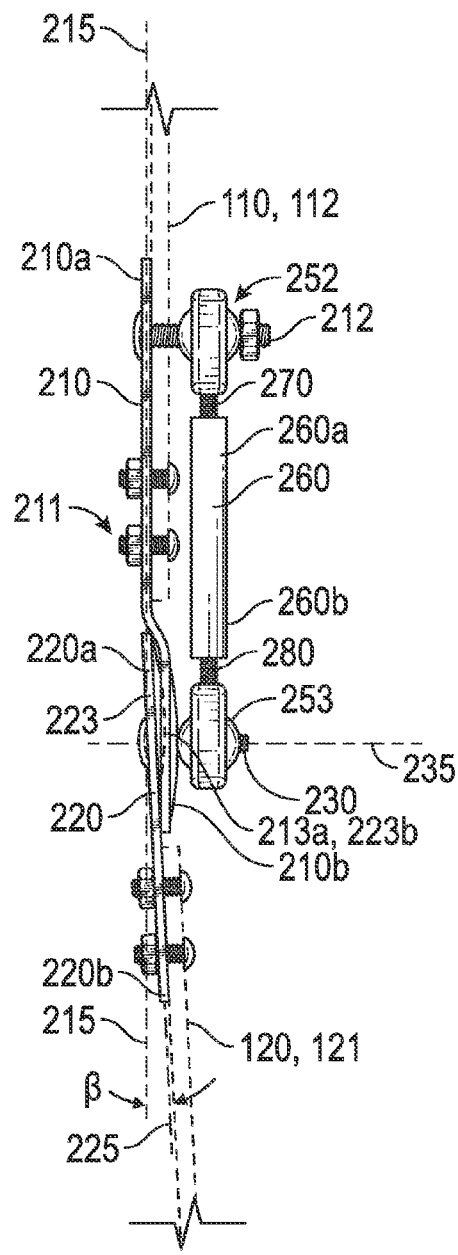
FIG. 10 is a front view of the hinge of FIG. 2 with the extension assembly in a retracted position and the lower arm angled laterally outward.

Referring specifically to FIGS. 9 and 10, the nested, overlapping relationship of plates 213, 223 may be adjusted to vary the position of pivot pin 230 within slot 214. Due to the mating, semi-spherical surfaces 213a, 223b of plates 213, 223, as pin 230 is moved downward in slot 214, end 220b of lower arm 220 pivots laterally inward relative to end 220a and upper arm 210, thereby defining a varus angle θ measured between axes 215, 225 in front view (FIG. 9). Further, as pin 230 is moved upward in slot 214, end 220b of lower arm 220 pivots laterally outward relative to end 220a and upper arm 210, thereby defining a valgus angle β measured between axes 215, 225 in front view (FIG. 10). As will be described in more detail below, extension assembly 250 may be lengthened or shortened to adjust and control the position of pin 230 within slot 214, thereby adjusting and controlling the angular orientation of upper arm 210 relative to lower arm 220 (i.e., varus angle θ and valgus angle β) in front view. However, regardless of the relative angular position of upper arm 210 relative to lower arm 220 (e.g., varus angle θ or valgus angle β), the mating, semi-spherical surfaces 213a, 223b of plates 213, 223 enable upper arm 210 to rotate about axis 235 relative to lower arm 220.

Referring again to FIGS. 5-10, the change in frontal plane angulation of lower arm 220 relative to upper arm 210 (i.e., varus angle θ and valgus angle β) is controlled by extension assembly 250, which extends between pins 212, 230. In particular, extension assembly 250 has a central axis 255, a first or upper end 250a, and a second or lower end 250b opposite first end 250a. First end 250a is connected to pin 212 with a first ball joint 252, and second end 250b is connected to pin 230 with a second ball joint 253. Ball joint 252 allows extension assembly 250 to simultaneously rotate and pivot inward and outward about pin 212. Similarly, ball joint 253 allows extension assembly 250 to simultaneously rotate and pivot inward and outward about pin 230. However, ball joints 252, 253 restrict ends 250a, b, respectively, from moving translationally relative to pins 212, 230, respectively.

Extension assembly 250 has a length $L_{250}$ measured axially (relative to axis 255) between ends 250a, b that is adjustable. Specifically, in this embodiment, extension assembly 250 includes a housing 260 coaxially aligned with axis 255, a first rod 270 extending axially from housing 260 to end 250a, and a second rod 280 extending axially from housing 260 to end 250b. Housing 260 has a first end 260a, a second end 260b opposite first end 260a, an internally threaded counterbore 261 extending axially from end 260a, and an internally threaded counterbore 262 extending axially from end 260b. Counterbores 261, 262 are oppositely threaded. For example, if internal threads of counterbore 261 are right-handed threads, then the internal threads of counterbore 262 are left-handed threads and vice versa. Rod 270 is threadingly received by counterbore 261, and rod 280 is threadingly received by counterbore 262. Thus, rods 270, 280 include external threads that mate and engage with the internal threads of counterbores 261, 262, respectively. Due to the oppositely threaded counterbores 261, 262, rotation of housing 260 about axis 255 relative to rods 270, 280 in a first direction causes rods 270, 280 to extend further from counterbores 261, 262, respectively, thereby increasing length $L_{250}$; and rotation of housing 260 about axis 255 relative to rods 270, 280 in a second direction opposite the first direction causes rods 270, 280 to retract further into counterbores 261, 262, respectively, thereby decreasing length $L_{250}$. To enable rotation of housing 260 relative to rods 270, 280 by a user of knee orthosis 100, the outer surface of housing 260 preferably includes a prismatic profile (e.g., octagonal, hexagonal, etc.) that facilitates gripping and rotation of housing 260.

As best shown in FIGS. 9 and 10, the length $L_{250}$ of extension assembly 250 may be adjusted to controllably vary the angular orientation of lower arm 220 relative to upper arm 210 (i.e., vary the angle between axes 215, 225 in front view). As length $L_{250}$ is increased, pin 230 is urged away from pin 212 through slot 214. Pin 230 slidingly engages slot 214 and is free to move through slot 214 relative to upper attachment plate 213, however, pin 230 is restricted from moving relative to lower attachment plate 223 as pin 230 extends through and engages bore 224 in lower attachment plate 223. Thus, as pin 230 is moved through slot 214, lower attachment plate 223 moves along with pin 230 relative to upper attachment plate 213. The interfacing semi-spherical interface surfaces 213a, 223b cause lower arm 220 to pivot medially inward relative to upper arm 210 in front view (i.e., in the frontal plane). If length $L_{250}$ is increased beyond the point at which axes 215, 225 are aligned in front view, referred to as the "neutral position," a varus angle θ is formed between arms 210, 220 (i.e., knee orthosis 100 defines a varus angle). On the other hand, as length $L_{250}$ is decreased, pin 230 is urged toward pin 212 through slot 214. As pin 230 is moved through slot 214, lower attachment plate 223 moves along with pin 230 relative to upper attachment plate 213. The interfacing semi-spherical interface surfaces 213a, 223b cause lower arm 220 to pivot laterally outward relative to upper arm 210 in front view (i.e., in the frontal plane). If length $L_{250}$ is decreased beyond the point at which axes 215, 225 are aligned in front view (i.e., the "neutral position") a valgus angle β is formed between arms 210, 220 (i.e., knee orthosis 100 defines a valgus angle). Although the angular orientation between arms 210, 220 in front view may be varied to achieve a desired varus angle θ or valgus angle β, ball joints 252, 253 enable arms 210, 220 to rotate and pivot relative to each other about axis 235. In other words, regardless of the angle between axes 215, 225 in front view, hinge joint 200 permits free flexion and extension about pivot pin 230 in the sagittal plane.

In general, the different components of the hinge joint (e.g., hinge joint 200) may comprise any suitable material(s) including, without limitation, metals or metal alloys (e.g., aluminum, steel, etc.), non-metals (e.g., plastic, ceramics, etc.), composites (e.g., carbon fiber epoxy matrix composite, etc.) or combinations thereof. However, the components of the hinge joint are preferably made from relatively rigid, durable, and lightweight material(s) such as aluminum or composites.

In the manner described, hinge joint 200 allows adjustment of the angle between arms 210, 220 in the frontal plane, while still allow flexion and extension in the sagittal plane. By adjusting this angle, knee orthosis 100 may be custom fit and utilized for treatment of varus or valgus knee conditions. Further, the angle between arms 210, 220 in the frontal plane may be adjusted by simply rotating housing 260—an operation a user or wearer of knee orthosis can perform by himself/herself.

In FIGS. 2-4, only a single hinge joint 200 is shown in knee orthosis 100 and positioned to be disposed along the lateral outside of the knee. However, in general, one hinge joint (e.g., hinge joint 200) may be provided on only one side of the knee (e.g., outside of the knee, or inside of the knee) or two hinge joints may be provided (e.g., one hinge joint disposed along the lateral outside and inside of the knee). For patient's with bilateral valgus deformities (knock-kneed), a single hinge joint disposed along the lateral outside of each knee is preferred to reduce the likelihood of inadvertent contact and engagement of laterally inner hinge joints.

Embodiments described herein provide a bi-axial hinge joint that is adjustable by the user to change the amount of varus or valgus in the orthosis. Consequently, embodiments described herein allow the user to (a) don the orthosis while the orthosis is positioned at the varus or valgus angle naturally present in the knee, and then (b) manually adjust the hinge joint of the orthosis to change the varus or valgus angle maintained by the orthosis, thereby applying corrective forces to the knee and/or leg in order to correct the deformity. The corrective forces operate to reduce the varus or valgus angulation to a lesser value (i.e., exert forces tending to move the knee joint to a more straight configuration). In addition, embodiments described herein allow for smooth flexion and extension after the corrective force is applied.

As compared to conventional devices, embodiments described herein offer the potential for numerous advantages. In particular, a user-adjustable hinge (that is, adjustable in the frontal plane) enables the patient to determine how much force is applied to their knee. Further, the user can obtain a better fit due to the sequence of first putting on a brace that matches the existing and natural knee angle, and after the brace is in place adjusting it to the desired angle to apply correction. Accordingly, embodiments described herein offer the potential to apply corrective forces on the knee joint to reduce pain and extend the life of the anatomical knee joint.

While preferred embodiments have been shown and described, modifications thereof can be made by one skilled in the art without departing from the scope or teachings herein. The embodiments described herein are exemplary only and are not limiting. Many variations and modifications of the systems, apparatus, and processes described herein are possible and are within the scope of the invention. For example, the relative dimensions of various parts, the materials from which the various parts are made, and other parameters can be varied. Accordingly, the scope of protection is not limited to the embodiments described herein, but is only limited by the claims that follow, the scope of which shall include all equivalents of the subject matter of the claims.

What is claimed is:

1. A knee orthosis, comprising:
    an upper leg attachment;
    a lower leg attachment;
    a hinge joint extending between the upper leg attachment and the lower leg attachment;
    wherein the hinge joint includes:
        an upper arm having a first end fixed to the upper leg attachment and a second end opposite the first end, the second end including a semi-spherical surface;
        a lower arm having a first end fixed to the lower leg attachment and a second end opposite the first end, the second end including a semi-spherical surface that mates with the semi-spherical surface of the second end of the upper arm;
        a first pin extending laterally through the semi-spherical surface of the lower arm and the semi-spherical surface of the upper arm, wherein the pin pivotally couples the upper arm to the lower arm;
        a second pin extending laterally through the upper arm;
        an extension coupling having a longitudinal axis, a first end pivotally and rotatably coupled to the first pin, and a second end pivotally and rotatably coupled to the second pin, wherein the extension coupling is adapted to increase the axial distance between the first pin and the second pin a first ball joint pivotally and rotatably connects the first end of the extension coupling to the first pin and a second ball joint pivotally and rotatably connects the second end of the extension coupling to the second pin.

2. The knee orthosis of claim 1, wherein the first pin extends through a borehole in the lower arm and an elongate slot in the upper arm.

3. The knee orthosis of claim 2, wherein the slot has a longitudinal axis that is parallel to the longitudinal axis of the extension coupling.

4. The knee orthosis of claim 1, wherein the extension coupling comprises:
a housing having a first end, a second end opposite the first end, a first counterbore extending axially from the first end, and a second counterbore extending axially from the second end;
wherein the first counterbore and the second counterbore are oppositely internally threaded;
a first rod extending axially from the first end of the housing to the first end of the extension coupling;
a second rod extending axially from the second end of the housing to the second end of the extension coupling;
wherein the first rod is threadingly received by the first counterbore and the second rod is threadingly received by the second counterbore.

5. The knee orthosis of claim 4, wherein the housing is adapted to rotate in a first direction about the longitudinal axis of the extension coupling to increase the axial length of the extension coupling, and is adapted to rotate in a second direction opposite the first direction about the longitudinal axis of the extension coupling to decrease the axial length of the extension coupling.

6. The knee orthosis of claim 1, wherein the semi-spherical surface of the upper arm is concave;
wherein the semi-spherical surface of the lower arm is convex; and
wherein the semi-spherical surface of the lower arm is received by the semi-spherical surface of the upper arm.

7. The knee orthosis of claim 6, wherein the semi-spherical surface of the upper arm is disposed along a medially inner side of the lower end of the upper arm, and the semi-spherical surface of the lower arm is disposed along a laterally outer side of the upper end of the lower arm.

8. The knee orthosis of claim 6, wherein the semi-spherical surface of the upper arm slidingly engages the semi-spherical surface of the lower arm.

9. The knee orthosis of claim 1, wherein the upper arm has a longitudinal axis and the lower arm has a longitudinal axis;
wherein the longitudinal axis of the upper arm is oriented at an angle relative to the longitudinal axis of the lower arm in a frontal plane;
wherein the extension coupling is adapted to adjust the angle in the frontal plane.

10. A knee orthosis, comprising:
an upper leg attachment;
a lower leg attachment;
a hinge joint extending between the upper leg attachment and the lower leg attachment;
wherein the hinge joint includes:
an upper arm having a first end fixed to the upper leg attachment and a second end opposite the first end, the second end including an attachment plate;
a lower arm having a first end fixed to the lower leg attachment and a second end opposite the first end, the second end including an attachment plate rotatably coupled to the attachment plate of the upper arm;
wherein the attachment plate of the upper arm includes an elongate slot, and the attachment plate of the lower arm includes a throughbore aligned with at least a portion of the elongate slot;
a first pin extending through the throughbore and the elongate slot;
an extension coupling having a longitudinal axis, a first end coupled to the first pin, and a second end pivotally and rotatably coupled to the upper arm, wherein the extension coupling is adapted to move the first pin through the elongate slot a first ball joint pivotally and rotatably connects the first end of the extension coupling to the first pin and a second ball joint pivotally and rotatably connects the second end of the extension coupling to the second pin.

11. The knee orthosis of claim 10, wherein the attachment plate of the upper arm includes a concave semi-spherical surface that receives a convex semi-spherical surface of the attachment plate of the lower arm.

12. The knee orthosis of claim 11, wherein the concave semi-spherical surface of the attachment plate of the upper arm is disposed along a medially inner surface of the attachment plate of the upper arm, and wherein the convex semi-spherical surface of the attachment plate of the lower arm is disposed along a laterally outer surface of the attachment plate of the lower arm.

13. The knee orthosis of claim 10, wherein the second end of the extension member is pivotally and rotatably coupled to the upper arm with a second pin extending through the upper arm.

14. The knee orthosis of claim 10, wherein the slot is aligned with the longitudinal axis of the extension coupling in lateral view.

15. The knee orthosis of claim 10, wherein the extension coupling comprises:
a housing having a first end, a second end opposite the first end, a first counterbore extending axially from the first end, and a second counterbore extending axially from the second end;
wherein the first counterbore and the second counterbore are oppositely internally threaded;
a first rod extending axially from the first end of the housing to the first end of the extension coupling;
a second rod extending axially from the second end of the housing to the second end of the extension coupling;
wherein the first rod is threadingly received by the first counterbore and the second rod is threadingly received by the second counterbore.

16. The knee orthosis of claim 15, wherein the housing is adapted to rotate in a first direction about the longitudinal axis of the extension coupling to increase the axial length of the extension coupling, and is adapted to rotate in a second direction opposite the first direction about the longitudinal axis of the extension coupling to decrease the axial length of the extension coupling.

17. The knee orthosis of claim 10, wherein the upper arm has a longitudinal axis and the lower arm has a longitudinal axis;
wherein the longitudinal axis of the upper arm is oriented at an angle relative to the longitudinal axis of the lower arm in a frontal plane;
wherein the extension coupling is adapted to adjust the angle in the frontal plane.

* * * * *